(12) United States Patent
Kerr et al.

(10) Patent No.: US 7,145,464 B2
(45) Date of Patent: Dec. 5, 2006

(54) DATA COLLECTION DEVICE

(75) Inventors: Roger S. Kerr, Brockport, NY (US);
Timothy J. Tredwell, Fairport, NY (US); Badhri Narayan, Rochester, NY (US); Diane M. Carroll-Yacoby, Honeoye Falls, NY (US)

(73) Assignee: Eastman Kodak Company, Rochester, NY (US)

( * ) Notice: Subject to any disclaimer, the term of this patent is extended or adjusted under 35 U.S.C. 154(b) by 412 days.

(21) Appl. No.: 10/717,369

(22) Filed: Nov. 19, 2003

(65) Prior Publication Data

US 2005/0107965 A1    May 19, 2005

(51) Int. Cl.
*G08B 17/12* (2006.01)
(52) U.S. Cl. .............. 340/600; 340/572.1; 713/186
(58) Field of Classification Search ............. 340/600, 340/572.1–572.9, 5.2, 825.54, 5.52, 5.53; 348/143, 156; 713/186
See application file for complete search history.

(56) References Cited

U.S. PATENT DOCUMENTS

| | | | |
|---|---|---|---|
| 3,580,565 A | 5/1971 | Mallory et al. ................ 271/39 |
| 3,713,148 A | 1/1973 | Cardullo et al. ......... 343/6.5 R |
| 3,835,301 A | 9/1974 | Barney .................... 235/61.11 |
| 4,075,018 A | 2/1978 | Custer ............................ 96/39 |
| 4,129,855 A | 12/1978 | Rodrian .................. 340/152 T |
| 4,178,183 A | 12/1979 | Ciurca, Jr. et al. .......... 430/553 |
| 4,208,210 A | 6/1980 | Sakai et al. ................. 430/140 |
| 4,247,758 A | 1/1981 | Rodrian ....................... 235/92 |
| 4,270,853 A | 6/1981 | Hatada et al. ................ 354/76 |
| 4,270,854 A | 6/1981 | Stemme et al. ............... 354/76 |
| 4,275,103 A | 6/1981 | Tsubusaki et al. .......... 428/148 |
| 4,394,441 A | 7/1983 | Kawaguchi et al. ........ 430/524 |
| 4,416,963 A | 11/1983 | Takimoto et al. ............. 430/69 |
| 4,418,141 A | 11/1983 | Kawaguchi et al. ........ 430/530 |
| 4,431,764 A | 2/1984 | Yoshizumi ................... 524/409 |
| 4,495,276 A | 1/1985 | Takimoto et al. ........... 430/527 |
| 4,571,361 A | 2/1986 | Kawaguchi et al. ........ 428/328 |
| 4,600,280 A | 7/1986 | Clark .......................... 352/37 |
| 4,663,625 A | 5/1987 | Yewen ................... 340/825.54 |
| 4,742,470 A | 5/1988 | Juengel ....................... 364/474 |
| 4,806,958 A | 2/1989 | Momot et al. ................ 354/21 |
| 4,855,769 A | 8/1989 | Slavitter et al. .............. 354/21 |
| 4,880,325 A | 11/1989 | Ueda et al. ................. 400/249 |

(Continued)

FOREIGN PATENT DOCUMENTS

JP    02-164872    6/1990

(Continued)

OTHER PUBLICATIONS

TEMIC Semiconductors, E5550-TK5550—Read/Write Transponder, pp. 1-7, www.eurochip.com/tec_server/tag/E5550%20Datasheet.pdf.

(Continued)

*Primary Examiner*—Phung T. Nguyen
(74) *Attorney, Agent, or Firm*—Roland R. Schindler, III

(57) ABSTRACT

In one aspect of the invention a data collection device is provided for use with a medium said medium being usable when exposed to electromagnetic radiation that is characteristic of such use. The data collection device has a sensor capable of sensing when the medium is exposed to electromagnetic radiation that is characteristic of such a use and generating an exposure signal in response thereto. A controller is connected to said sensor and stores data in a memory when an exposure signal is detected.

39 Claims, 2 Drawing Sheets

U.S. PATENT DOCUMENTS

| | | | |
|---|---|---|---|
| 4,905,029 A | 2/1990 | Kelley | 354/76 |
| 4,983,996 A | 1/1991 | Kinoshita | 354/76 |
| 4,990,092 A | 2/1991 | Cummings | 434/317 |
| 4,999,276 A | 3/1991 | Kawabaa et al. | 430/264 |
| 5,008,661 A | 4/1991 | Raj | 340/825.54 |
| 5,019,815 A | 5/1991 | Lemelson et al. | 340/933 |
| 5,030,544 A | 7/1991 | Olbrechts et al. | 430/140 |
| 5,049,898 A | 9/1991 | Arthur et al. | 346/1.1 |
| 5,049,904 A | 9/1991 | Nakamura et al. | 346/140 R |
| 5,059,126 A | 10/1991 | Kimball | 434/308 |
| 5,078,523 A | 1/1992 | McGourty et al. | 400/613 |
| 5,104,247 A | 4/1992 | Ohshima | 400/240.3 |
| 5,105,190 A | 4/1992 | Kip et al. | 340/825.54 |
| 5,122,445 A | 6/1992 | Ishigaki | 430/523 |
| 5,184,152 A | 2/1993 | French | 346/76 PH |
| 5,185,315 A | 2/1993 | Sparer | 503/227 |
| 5,196,846 A | 3/1993 | Brockelsby et al. | 340/933 |
| 5,196,862 A | 3/1993 | Fisher, Sr. | 346/7.6 PH |
| 5,224,784 A | 7/1993 | Haftmann et al. | 400/208 |
| 5,266,968 A | 11/1993 | Stephenson | 346/76 PH |
| 5,266,975 A | 11/1993 | Mochizuki et al. | 346/140 R |
| 5,268,708 A | 12/1993 | Harshbarger et al. | 346/134 |
| 5,290,190 A | 3/1994 | McClanahan | 434/317 |
| 5,294,525 A | 3/1994 | Yamauchi et al. | 430/523 |
| 5,297,881 A | 3/1994 | Ishiyama | 400/705 |
| 5,300,575 A | 4/1994 | Jonas et al. | 525/186 |
| 5,305,020 A | 4/1994 | Gibbons et al. | 346/76 PH |
| 5,310,999 A | 5/1994 | Claus et al. | 235/384 |
| 5,312,681 A | 5/1994 | Muys et al. | 428/323 |
| 5,313,235 A | 5/1994 | Inoue et al. | 354/76 |
| 5,318,370 A | 6/1994 | Nehowig | 400/613 |
| 5,323,704 A | 6/1994 | Fraczek | 101/375 |
| 5,331,338 A | 7/1994 | Mager | 346/108 |
| 5,340,676 A | 8/1994 | Anderson et al. | 430/63 |
| 5,342,671 A | 8/1994 | Stephenson | 428/195 |
| 5,347,274 A | 9/1994 | Hassett | 340/988 |
| 5,354,613 A | 10/1994 | Quintens et al. | 428/341 |
| 5,365,312 A | 11/1994 | Hillmann et al. | 355/206 |
| 5,368,995 A | 11/1994 | Christian et al. | 430/530 |
| 5,370,981 A | 12/1994 | Krafft et al. | 430/529 |
| 5,372,924 A | 12/1994 | Quintens et al. | 430/527 |
| 5,382,494 A | 1/1995 | Kudo et al. | 430/140 |
| 5,385,416 A | 1/1995 | Maekawa et al. | 400/203 |
| 5,391,472 A | 2/1995 | Muys et al. | 430/527 |
| 5,398,257 A | 3/1995 | Groenteman | 375/200 |
| 5,403,467 A | 4/1995 | Jones et al. | 205/125 |
| 5,426,011 A | 6/1995 | Stephenson | 430/22 |
| 5,430,441 A | 7/1995 | Bickley et al. | 340/825.54 |
| 5,443,944 A | 8/1995 | Krafft et al. | 430/529 |
| 5,455,617 A | 10/1995 | Stephenson et al. | 347/214 |
| 5,459,021 A | 10/1995 | Ito et al. | 430/527 |
| 5,466,576 A | 11/1995 | Schulz et al. | 435/6 |
| 5,484,694 A | 1/1996 | Lelental et al. | 430/530 |
| 5,491,327 A | 2/1996 | Saroya | 235/449 |
| 5,491,468 A | 2/1996 | Everett et al. | 340/572 |
| 5,493,385 A | 2/1996 | Ng | 355/326 |
| 5,504,507 A | 4/1996 | Watrobski et al. | 347/19 |
| 5,513,920 A | 5/1996 | Whritenor et al. | 400/246 |
| 5,516,590 A | 5/1996 | Olmstead et al. | 428/484 |
| 5,521,663 A | 5/1996 | Norris, III | 354/106 |
| 5,528,222 A | 6/1996 | Moskowitz et al. | 340/572 |
| 5,528,377 A | 6/1996 | Hutcheson | 358/298 |
| 5,530,702 A | 6/1996 | Palmer et al. | 370/85.3 |
| 5,532,727 A | 7/1996 | Agano et al. | 347/253 |
| 5,537,920 A | 7/1996 | Hasegawa et al. | 101/116 |
| 5,547,501 A | 8/1996 | Maruyama et al. | 106/21 R |
| 5,559,578 A | 9/1996 | Umeda et al. | 355/208 |
| 5,562,352 A | 10/1996 | Whritenor et al. | 400/242 |
| 5,565,906 A | 10/1996 | Schoon | 347/248 |
| 5,574,519 A | 11/1996 | Manico et al. | 396/429 |
| 5,575,898 A | 11/1996 | Wolf et al. | 205/125 |
| 5,584,070 A | 12/1996 | Harris et al. | 455/346 |
| 5,598,201 A | 1/1997 | Stodder et al. | 347/104 |
| 5,600,350 A | 2/1997 | Cobbs et al. | 347/19 |
| 5,600,352 A | 2/1997 | Knierim et al. | 347/40 |
| 5,606,347 A | 2/1997 | Simpson | 345/187 |
| 5,610,635 A | 3/1997 | Murray et al. | 347/7 |
| 5,620,265 A | 4/1997 | Kondo | 400/196 |
| 5,625,391 A | 4/1997 | Hirabayashi et al. | 347/41 |
| 5,644,557 A | 7/1997 | Akamine et al. | 369/14 |
| 5,647,679 A | 7/1997 | Green et al. | 400/232 |
| 5,661,515 A | 8/1997 | Hevenor et al. | 347/215 |
| 5,700,623 A | 12/1997 | Anderson et al. | 430/256 |
| 5,713,288 A | 2/1998 | Frazzitta | 101/492 |
| 5,721,992 A | 2/1998 | Chovanes | 396/312 |
| 5,755,519 A | 5/1998 | Klinefelter | 400/249 |
| 5,757,021 A | 5/1998 | Dewaele | 250/587 |
| 5,757,394 A | 5/1998 | Gibson et al. | 347/19 |
| 5,768,633 A | 6/1998 | Allen et al. | 396/2 |
| 5,774,639 A | 6/1998 | Schildkraut et al. | 395/115 |
| 5,774,752 A | 6/1998 | Patton et al. | 396/312 |
| 5,790,216 A | 8/1998 | Inbar et al. | 349/83 |
| 5,812,156 A | 9/1998 | Bullock et al. | 347/19 |
| 5,842,118 A | 11/1998 | Wood, Jr. | 455/101 |
| 5,850,481 A | 12/1998 | Rhoads | 382/232 |
| 5,875,249 A | 2/1999 | Mintzer et al. | 380/54 |
| 5,912,972 A | 6/1999 | Barton | 380/23 |
| 5,913,088 A | 6/1999 | Moghadam et al. | 396/311 |
| 5,914,671 A | 6/1999 | Tuttle | 340/825.54 |
| 5,949,885 A | 9/1999 | Leighton | 380/54 |
| 6,031,516 A | 2/2000 | Leiper | 345/115 |
| 6,031,914 A | 2/2000 | Tewfik et al. | 380/54 |
| 6,044,156 A | 3/2000 | Honsinger et al. | 380/54 |
| 6,075,950 A | 6/2000 | Stephenson | 396/312 |
| 6,096,491 A | 8/2000 | Majumdar et al. | 430/529 |
| 6,099,178 A | 8/2000 | Spurr et al. | 400/207 |
| 6,106,166 A | 8/2000 | Spurr et al. | 396/578 |
| 6,124,083 A | 9/2000 | Majumdar et al. | 430/529 |
| 6,157,373 A | 12/2000 | Rego | 345/173 |
| 6,173,119 B1 | 1/2001 | Manico et al. | 396/6 |
| 6,227,643 B1 | 5/2001 | Purcell et al. | 347/19 |
| 6,263,310 B1 | 7/2001 | Loudermilk et al. | 704/272 |
| 6,282,819 B1 | 9/2001 | Gu | 40/124.03 |
| 6,353,672 B1 | 3/2002 | Rhoads | 382/100 |
| 6,496,595 B1 * | 12/2002 | Puchek et al. | 382/124 |
| 6,720,874 B1 * | 4/2004 | Fufido et al. | 340/541 |
| 6,774,782 B1 * | 8/2004 | Runyon et al. | 340/505 |
| 6,794,986 B1 * | 9/2004 | Puchek et al. | 340/5.53 |
| 6,963,659 B1 * | 11/2005 | Tumey et al. | 382/116 |
| 2002/0101619 A1 | 8/2002 | Tsubaki et al. | 358/302 |

FOREIGN PATENT DOCUMENTS

| | | |
|---|---|---|
| JP | 06-044265 | 7/1992 |
| NL | 9400392 | 3/1994 |
| WO | WO 98/52762 | 11/1998 |

OTHER PUBLICATIONS

TEMIC Semiconductors, e5550—Standard Read/Write Identification IC, Rev. A3, Mar. 17, 1998, pp. 1-11.

HID Corp., Multi-Technology Card Guide, pp. 1, www.hidcorp.com/products.

HID Corp., ProxCard® II, Proximity Access Card, pp. 1-2, www.hidcorp.com/products.

HID Corp., ISO Thin Card, pp. 1-2, www.hidcorp.com/products.

Protective Security Management, HID Prox Cards, pp. 1, www.prosecman.com.au.

Atmel Corp., Atmel Smart Card ICs, 2000, pp. 1-12.

Texas Instruments, Tag-it™ —Moving Concepts to Reality, pp. 1-13, 2000.

Texas Instruments, Making RFID work for you: An Industry Roundtable hosted by Texas Instruments at NACS-Tech 1998, 2000, pp. 1-15, www.ti.com/tiris.

Texas Instruments, d'Hont, The Cutting Edge of RFID Technology and Applications for Manufacturing and Distribution, pp. 1-13, www.ti.com/tiris.

Atmel Corp., Atmel Read-Only Transponder—TK5530, Rev. A5, Dec. 19, 2001, pp. 1-10, www.atmel-wn.com.

Philips Semiconductors, mifare Standard Card IC MFI IC S50 Functional Specification, Rev. 5.1, May 2001, pp. 1-19, www.semiconductors.philips.com.

Texas Instruments, Radio Frequency Identification Systems—Access Control, pp. 1-2, www.ti.com/tiris/docs/solutions/solutions.shtml.

Texas Instruments, Michael Knebelkamp, et al., Latest Generation Technology for Immobilizer Systems, www.ti.com/tiris.

* cited by examiner

DATA COLLECTION DEVICE

FIELD OF THE INVENTION

The present invention generally relates to the field of mediums and more particularly to mediums that provide an indication of use.

BACKGROUND OF THE INVENTION

Mediums having images or information thereon or therein such as motion picture films, x-ray films, film negatives, documents, legal or otherwise, are subject to a variety of uses such as viewing, exposing, projecting, scanning, and/or copying. Conventionally, such mediums do not provide any capacity for providing tracking information indicating that such a medium has been so used, how many times the medium has used, who used the medium, how the medium was used, and where the medium was used. This presents a potential security risk in that any person possessing such medium can make unauthorized use of the medium. Thus, what is needed is a device for use with a medium that enables data to be recorded in association with the medium to indicate use of the medium.

Such a combination of medium devices has many valuable applications, for example, in Hospital Information Systems (HIS) or Radiology Information Systems (RIS) to track the use of patient medical records data for patients admitted to hospitals or receiving outpatient care so that the patients privacy can be properly maintained. By using such a combination, information such as who has viewed a patients x-ray films or how many copies of an original document have been made can be determined from the original copy. This can help to ensure privacy and help to obtain the proper medical care, without jeopardizing quality and timeliness. Similarly, access and use of confidential legal and financial records can be tracked in like manner.

In other applications, the motion picture industry could benefit also by knowing how many times a motion picture has been viewed or if the motion picture had been scanned in a way that would indicate an illegal copy had been made.

Thus, it can be seen that there is a need to be able tell if a medium has been viewed, exposed, scanned or photo copied.

Document management systems are known that track document movement by associating a tracking memory such as a bar code or Radio Frequency Identification (RFID) tag with each document. In these systems, the movement and use of the documents having a tracking memory monitored by specially adapted readers that detect the use of the document and stores data characterizing the use of the document. However, such a system is useful only where the documents must be used in a manner that triggers such a reader. Other use of the document will not be detected or recorded. For example if a document is copied using a copier that is not adapted with a reader, the copying of the document will not be recorded.

Thus, what is needed is the ability to monitor use of a medium that can indicate that a medium has been viewed, exposed, scanned, photo copied or otherwise used, but that does not depend upon the use of the medium in conjunction with a specially adapted device.

SUMMARY OF THE INVENTION

In one aspect of the invention a data collection device is provided for use with a medium said medium being usable when exposed to electromagnetic radiation that is characteristic of such use. The data collection device has a sensor capable of sensing when the medium is exposed to electromagnetic radiation that is characteristic of such a use and generating an exposure signal in response thereto. A controller is connected to said sensor and stores data in a memory when an exposure signal is detected.

In another aspect of the invention, a data collection device is provided. The device has a web of medium said medium being useable when the medium is subject to an exposure to light that is within a predefined range of exposures; a light sensor sensing exposure of the medium to light, a memory and a controller. The controller is connected to said light sensor and stores information in the memory indicative of an exposure when the medium is subject to a light exposure that is within the range.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

The present invention is directed in particular to elements forming part of, or cooperating more directly with, an apparatus in accordance with the invention. It is to be understood that elements not specifically shown or described may take various forms well known to those skilled in the art.

Figure 1:
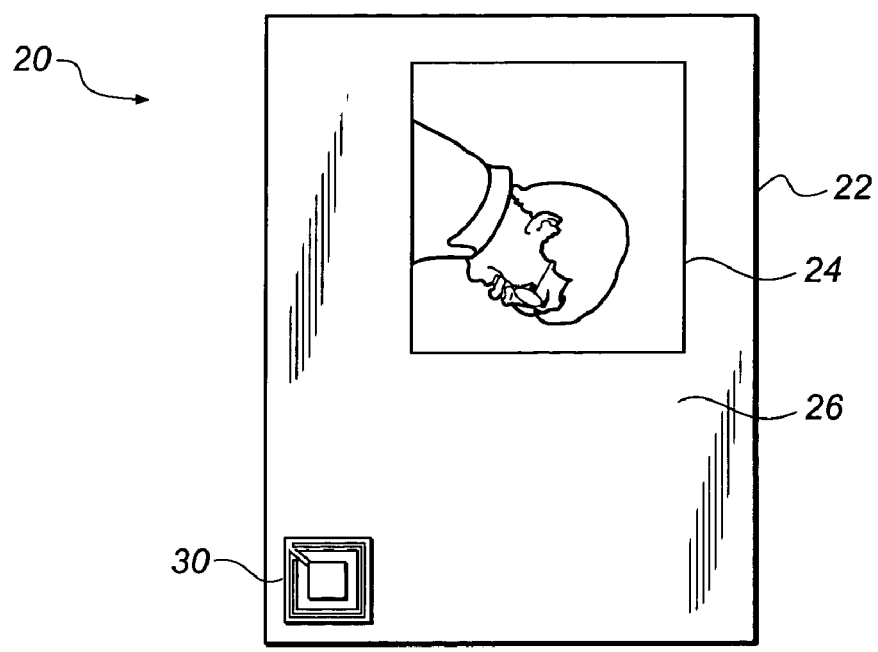
FIG. 1 shows a plan view of a medium substrate having an image thereon and a data collection device of the present invention.

FIG. 1 shows a first embodiment of a medium 20 having a data collection device 30 in accordance with the present invention. As is shown in FIG. 1, medium 20 comprises a medium substrate 22 having recorded image content 24 thereon such as an image, text, graphics or other encodement. Medium substrate 22 can be formed from a material such as paper, plastic, metal, fabric, or other convenient substrate known in the art. Medium substrate 22 can be adapted to receive image content 24 in the form of a donor material that is applied, for example, by spraying, thermally applying or otherwise deposited on an outer surface 26 of medium substrate 22. Medium substrate 22 can also comprise, for example, a photosensitive film or other material that is sensitive to electro magnetic radiation. When such a photosensitive film or other material are later subject to a photoprocessing step, image dyes and/or silver becomes visible on the film. Other types of medium substrates 22 that can bear image content 24 can be used and medium substrate 22 and image content 24 can comprise, for example, films, motion picture films, film negatives, documents, film transparences, fabrics, photographic prints, artwork, printed objects, or any other image graphics or text but not limited thereto.

In the embodiment shown, data collection device 30 is joined to medium substrate 22 by way of mechanical fasteners, adhesives or other known means of association or mechanically joining a device to medium substrate 22. Alternatively, data collection device 30 can be stored on, embedded in or otherwise provided within medium substrate 22 using techniques described in commonly assigned U.S. patent application Ser. Nos. 10/256,769, 10/256,824, and/or Ser. No. 10/411,624. In one embodiment, data collection device 30 comprises a substrate (not shown). The substrate is then joined to medium 20. The substrate can have an adhesive layer thereon which can be used for this purpose. Prior to assembly of data collection device 30 and medium 20, a removable covering or label can be applied over the adhesive to provide a so-called peel-and-stick form of data collection device 30. In this regard, medium data collection device 20 can be made small and can, for example, be within a range of 10×10×10 microns to 100×400×500 microns.

Figure 2:
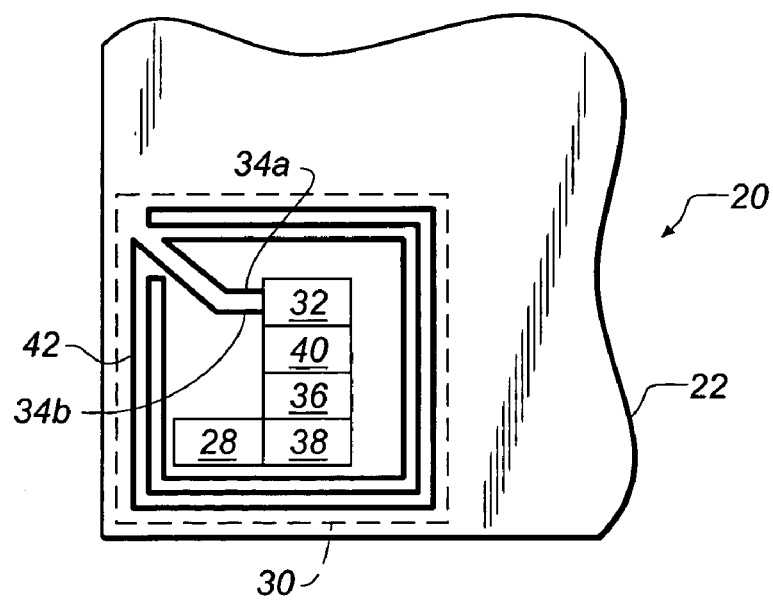
FIG. 2 shows a cutaway view of a medium substrate having a data collection device of the present invention.

FIG. 2 shows a cutaway view of medium data collection device 20 having one embodiment of a data collection device 30 in accordance with the present invention. As a shown the embodiment of FIG. 2, data collection device 30 comprises a communication circuit 32 that is connected to an antenna 42 via leads 34*a* and 34*b*, a control circuit 36, a memory 38, and an electromagnetic sensor 40.

In a preferred embodiment, data collection device 30 is a relatively low-power device that derives its source power from electromagnetic radiation collected by electromagnetic sensor 40. In this regard, electromagnetic sensor 40 can be adapted to collect energy from electromagnetic radiation directed at the medium data collection device 30 and to convert this collected electromagnetic radiation into power that operates data collection device 30. Alternatively, data collection device 30 can be equipped with a power supply 28 such as a chemical battery or a capacitive energy storage unit. In still another embodiment, data collection device 30 can additionally be powered by electrical energy collected by communication circuit 32. These latter alternatives allow the operation of data collection device 30 under circumstances wherein the electromagnetic radiation directed at medium data collection device 20 is insufficient to allow power from electromagnetic sensor 40 to operate data collection device 30.

In operation, data collection device 30 is activated when electromagnetic sensor 40 senses electromagnetic radiation directed at medium 20 that is characteristic of a use of the medium. For example, medium 20 can be photosensitive film that records images when subjected to a range of exposures to a form of electromagnetic radiation such as visible light or non-visible light such as infrared light, ultra-violet light and x-rays. In such a case, electromagnetic sensor 40 will detect an exposure of medium 20 to light that is within the range of exposure that the film is sensitive to. Alternatively, medium 20 can have image content 24 recorded thereon with image content 24 being useable for purposes such as copying, projection, photographic reproduction, electro-photographic reproduction, scanning or other uses when image content 24 is subject to an exposure to light or other electromagnetic radiation that is characteristic of such use. Here too, sensor 40 can be adapted to detect such a characteristic exposure.

In one embodiment, the characteristic exposure can be defined as an exposure to electromagnetic radiation having an intensity that is within a predefined range suitable for using the recorded image content 24 carried by medium substrate 22. The predefined range of electromagnetic radiation can be any level of electromagnetic radiation that permits accurate use of the recorded image content 24 on medium substrate 22. This predefined range can vary based upon the type of medium substrate 22, and the desired level of accuracy. For example, the predefined range of electromagnetic radiation exposure can be defined as a range that is any level sufficient for human observation of the recorded image content 24 on medium substrate 22. Alternatively, the predefined range of electromagnetic radiation exposure can be defined as a range that is sufficient for machine or other automatic use of the recorded image content 24 on medium substrate 22. For specific media, such as a motion picture film, the predefined range of electromagnetic radiation exposure can be defined as one that is sufficient, for example, to form an image on an unexposed film or to support projection of the recorded image content 24 on motion picture film for use in exhibition of the motion picture film. In this way, the number of times a motion picture film has been exhibited can be tracked.

It will be appreciated that, in this example, the electromagnetic radiation exposure level used for projection is substantially higher than the level used to which the film is exposed during normal handling such as from daylight or conventional interior lighting. Accordingly, mere handling of the motion picture film under conventional ambient lighting conditions will not trigger electromagnetic sensor 40.

The electromagnetic radiation that electromagnetic sensor 40 is sensitive to can take many forms. For example, the electromagnetic radiation can comprise any visible light, infrared light radiation, or ultraviolet light radiation. Other forms of electromagnetic radiation can also be sensed. In this regard, electromagnetic sensor 40 will be adapted to sense one or more preferred form of electromagnetic radiation e.g. visible light and to determine when medium 20 has been exposed to a predetermined level of the at least one preferred form of electromagnetic radiation. Electromagnetic sensor 40 can also detect patterns of exposure intensities over time to identify a characteristic exposure.

Electromagnetic sensor 40 provides an exposure signal to controller 36 indicating that medium substrate 22 has been subjected to the characteristic exposure. electromagnetic radiation within the predetermined range of exposures. Controller 36 generates data indicating that medium 20 has been exposed and stores this data in memory 38. Controller 36 can maintain a record of the number of exposures electromagnetic sensor 40 has detected. However, controller 36 can generate other information. This other information can comprise, for example information indicating the length of each exposure, information indicating the date and time of exposure. In this regard, controller 36 can include a timer for measuring the length of each exposure and/or a clock encounter system for determining a date and time of exposure.

Figure 3:
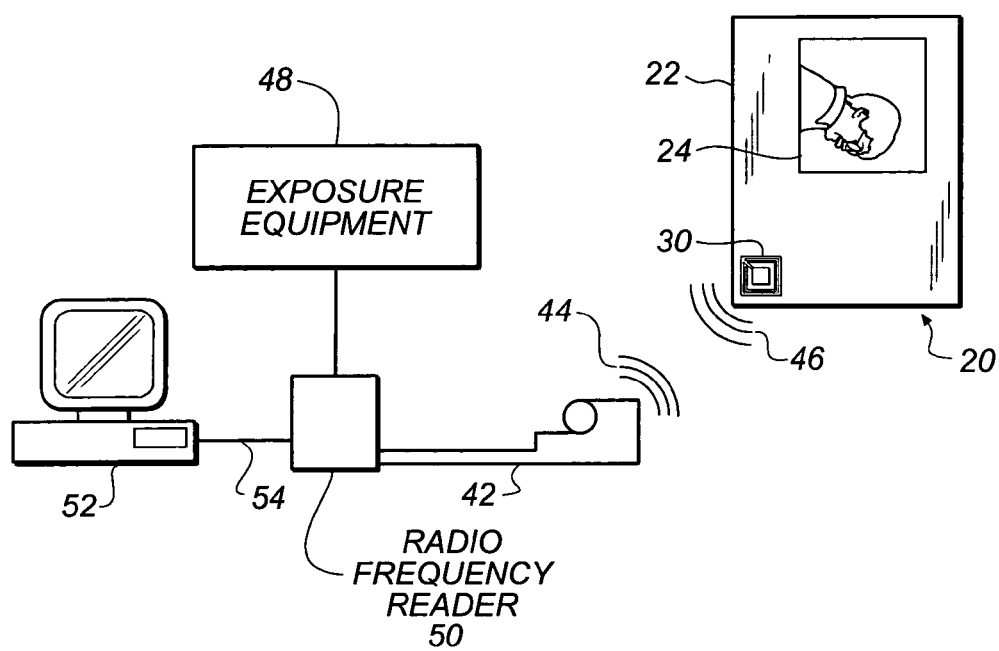
FIG. 3 shows an illustration of a media data collection device communicating with a radio frequency read write device of the present invention.

Referring to FIG. 3, data collection device 30 can also obtain information from the environment surrounding medium data collection device 20 to determine information such information indicating the location of each exposure and or indicating the equipment or processes by which the exposure has been made. In this regard, data collection device 30 associated with medium 20 can use communication circuit 32 to generate a first electromagnetic magnetic field 44 optionally containing identifying data to a radio frequency reader 50 that is associated with exposure equipment 48 used for making the exposure. Reader 50 responds to first electromagnetic field 44 with a second electromagnetic field 46 having data stored therein such as data that identifies persons who are proximate to the medium data collection device 20 at the time of exposure, exposure equipment 43, the location of exposure, and/or the processes by which exposure equipment 48 made the exposure. This data can be stored in memory 38 by control circuit 36.

In another embodiment radio frequency reader 50 generates a first electromagnetic field 44 that radiates into an area proximate to data collection device 30, which in turn responds with a second electromagnetic field identifying medium 20 and receives information such as, persons who are proximate to the medium at the time of exposure, location of exposure, and/or the processes by which the equipment made the exposure which can be stored in memory 38 by controller 36 from radio frequency reader 50. In still another embodiment, the electromagnetic radiation sensed by electromagnetic radiation sensor 40 could itself be modulated to contain data that can be detected by sensor 40 and stored in memory 38 by control circuit 36.

In the embodiment shown in FIG. 3, radio frequency reader 50 is shown connected to a computer 52 having a database or connected to a network having a database. Radio frequency reader 50 also connects to an antenna 42. The radio frequency reader 50 and antenna 42 serve as an interface allowing the computer 52 to communicate with memory 32 by control circuit 36. Radio frequency reader 50 is electrically coupled to computer 52, by means of a signal interface 54. Signal interface 54 may be, for example, a standard RS-232C serial connection, a Universal Serial Bus connection, or other type of signal interface known to those of skill in the art. This allows computer 52 to control the operation of radio frequency reader 50 so that radio frequency reader 50 can successively poll one or more medium data collection device 20 in order to selectably access information about one or more medium data collection device 20. Computer 52, which may be a standard personal computer or other programmable logic device is programmed to cause radio frequency reader 50 to read data that is stored in memory 32 of data collection device 30 and then to render an output based upon the stored data. This output can be, for example, a database useful in tracking use of medium 20 in adjusting exposure equipment 48 and for other purposes. Computer 52 can also cause data collection device 30 to store data in memory 32 of a selected data collection device 30.

It is important to note that computer 52 can alternately be joined with audio frequency reader 50 in the form of a unitary "hand-held" device. Using this alternate arrangement, an operator can associate information with data collection device 30 fixed to recording 24 or decode information that has already been stored in the memory 32 of such a data collection device 30 without requiring connection to a separate computer 52. This arrangement would be advantageous, for example, for portable data gathering or annotation purposes.

As noted above, one particular application of such a data collection device 30 can be found in the medical industry. For example, the privacy of confidential medical records is a paramount importance in providing effective and timely medical care. Policies at medical facilities and legal requirements typically dictate that only designated positions and staff members are allowed access to particular diagnostic images and other patient information. By providing medical records that are each associated with a data collection device 30, unauthorized use or copying of the medical records can be quickly detected. This has the effect of deterring unauthorized uses of the records. Even when such use is not deterred, the data obtained by data collection device 30 can be used to provide forensic information that can be used to trace and identify persons making such unauthorized copies.

In other particular application of such a data collection device 30 can be found to motion picture industry. In this industry, valuable intellectual property is recorded on a photosensitive films. Here too, when such films are associated with a data collection device 30, unauthorized use or copying of the films can be quickly detected which has a deterrent effect. Even when such use is not deterred, the data obtained by data collection device 30 can be used to provide forensic information that can be used to trace persons making such unauthorized copies. The use of such a data collection device 30 provide other benefits in motion picture industry in that the data stored in data collection device 30 can be extracted when a motion picture print is returned to a distributor for destruction or redistribution at the end of an exhibition run. This information can be used to confirm the authenticity of the print that has been destroyed and/or obtain information about the use of the prints. In such an application, data collection device can be incorporated into the film print within an area that is illuminated directly during use or in an area that is illuminated indirectly during use such as an area that is adjacent to a directly illuminated area and that receives a fraction of the light from use.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

PARTS LIST 20 medium
22 medium substrate
24 image content
26 outer surface
28 power supply
30 data collection device
32 communication circuit
34a lead
34b lead
36 control circuit
38 memory
40 electromagnetic sensor
42 antenna
44 first electromagnetic field
46 second electromagnetic field
48 exposure equipment
50 radio frequency reader
52 computer
54 signal interface

What is claimed:

1. A data collection device comprising:
   a sensor adapted for use with a medium that is usable when exposed to electromagnetic radiation of predetermined characteristic, said sensor being capable of sensing when the medium is exposed to electromagnetic radiation of said predetermined characteristic and of generating an exposure signal in response thereto;
   a memory; and
   a controller connected to said sensor and adapted to store data in the memory when an exposure signal is generated.

2. The data collection device of claim 1, wherein electromagnetic radiation comprises at least one of a radio frequency signal, a visible light, and a non-visible light.

3. The data collection device of claim 1, wherein the sensor collects energy from the electromagnetic radiation so that the sensor, controller and memory can be operated using the collected energy.

4. The data collection device of claim 1, wherein the electromagnetic radiation sensor capable of generating an exposure signal when the medium is exposed to electromagnetic radiation that is within a predetermined range of electromagnetic radiation intensities.

5. The data collection device of claim 1, wherein the sensor is adapted to sense a characteristic exposure comprising a pattern of electromagnetic radiation intensities over a period of time and to generate an exposure signal when the pattern is sensed.

6. The data collection device of claim 1, wherein the sensor senses a characteristic exposure comprising pattern of electromagnetic radiation intensities over a period of time with the pattern of electromagnetic radiation indicating that the medium is being illuminated for at least one of an initial exposure, printing, projection, photographic, electro-photographic, scanning or image reproduction purposes.

7. The data collection device of claim 1, wherein the electromagnetic radiation sensor senses that the medium has been subjected to electromagnetic radiation intensities that correlate to exposure of the medium at a range of exposure that is above a minimum threshold for projection, photographic reproduction, electro-photographic, scanning or image reproduction purposes.

8. The data collection device of claim 1, wherein the controller stores data in the memory indicating at least one of the length of exposure, the pattern of exposure intensities over time, the number of exposures, the date and time of exposure, the location of exposure, and the equipment used for exposure.

9. The data collection device of claim 1, wherein the electromagnetic radiation includes data that identifies at least one of a viewer proximate to the data collection device, the source of the electromagnetic radiation, a location, a time and information characterizing the use of the medium and wherein when the controller stores the digital data in the memory in response to each exposure signal.

10. The data collection device of claim 1, further comprising a communication circuit adapted to receive a first electromagnetic signal and to generate a second electromagnetic field in the memory.

11. The data collection device of claim 1, wherein the sensor comprises an electromagnetic radiation sensor having a charge cycle that generates an exposure signal each time that the charge cycle is completed and discharged.

12. The data collection device of claim 1, wherein the source of the electromagnetic radiation source is a diagnostic illumination device used to view medical films.

13. The data collection device of claim 1, wherein the source of electromagnetic radiation is a film projector.

14. The data collection device of claim 1, wherein the source of electromagnetic radiation is a film printer.

15. The data collection device of claim 1, wherein the source of electromagnetic radiation is a film scanner.

16. The data collection device of claim 1, wherein the source of electromagnetic radiation is a document copier.

17. The data collection device of claim 1, wherein the medium is an x-ray film.

18. The data collection device of claim 1, wherein the medium is a motion picture film.

19. The data collection device of claim 1, further comprising a communication circuit generating a warning signal when the controller detects an exposure signal the warning signal indicating that the document is not to be used.

20. The data collection device of claim 1, wherein the data collection device comprises a substrate supporting the sensor, memory and controller.

21. The data collection device of claim 20, wherein the substrate has an adhesive layer for joining the data collection device to a medium.

22. The data collection device of claim 1, wherein the medium is the substrate.

23. The data collection device of claim 1, wherein the medium is formed about the data collection device.

24. The data collection device of claim 1, wherein the data collection device is joined to the medium.

25. The data collection device of claim 1, wherein, the data collection device is sized between 10×10×10 microns and 100×400×500 microns.

26. The data collection device of claim 1, wherein the medium is an image recording medium that records images in response to a characteristic exposure of the medium to a light and the sensor is adapted to sense the characteristic exposure.

27. The data collection device of claim 1, wherein the medium is an image bearing medium that having images that are viewable only in response to a characteristic exposure of the medium to a light and wherein the sensor is adapted to sense the characteristic exposure.

28. The data collection device of claim 1, wherein the medium is an image recording medium that records images in response to a characteristic exposure of the medium to a light.

29. A data collection device, comprising:
  a web of medium, said medium being useable when the medium is subject to an exposure to light that is within a predefined range of exposure;
  a light sensor sensing exposure of the medium to light;
  a memory; and
  a controller connected to said light sensor and storing information in the memory indicative of an exposure when the medium is subject to a light exposure that is within the range.

30. The data collection device of claim 29, wherein the exposure range is sufficient for accurate use of the image comprises a level sufficient for human observation of the image.

31. The data collection device of claim 30, wherein the exposure range is sufficient for exposing images onto unexposed film.

32. The data collection device of claim 29, wherein the exposure range is sufficient for accurate use of the image comprises a level sufficient for automatic reproduction of the image.

33. The data collection device of claim 29, wherein the exposure range is sufficient for scanning processed film.

34. The data collection device of claim 33, wherein the communication circuit comprises a radio-frequency transponder circuit.

35. The data collection device of claim 33, wherein the communication circuit generates a warning signal each time that the image is exposed to light at the exposure level that is sufficient for accurate use of the image.

36. The data collection device of claim 33 wherein the communication circuit is adapted to receive a signal having data stored.

37. The data collection device of claim 29, further comprising a communication circuit permitting communication between the memory and an external device.

38. The data collection device of claim 29, wherein light sensor detects exposure of the image only to selected wavelengths of light.

39. The data collection device of claim 29 wherein the memory contains information that can be used to authenticate the medium.

* * * * *